United States Patent [19]

Kearnes et al.

[11] Patent Number: 4,857,240
[45] Date of Patent: Aug. 15, 1989

[54] FRAGRANCE VAPOR DISPENSER MOUNTING BRACKET

[75] Inventors: Thom Kearnes, Akron; Joel Wennerstrom, Streetsboro; William Glover, Chesterland, all of Ohio

[73] Assignee: The State Chemical Mfg. Co., Cleveland, Ohio

[21] Appl. No.: 229,838

[22] Filed: Aug. 8, 1988

[51] Int. Cl.$^4$ .............................................. B01F 3/04
[52] U.S. Cl. ...................................... 261/26; 261/30; 261/DIG. 65; 422/124; 239/60
[58] Field of Search ................... 261/30, DIG. 65, 26; 422/124; 239/35, 57, 60

[56] References Cited

U.S. PATENT DOCUMENTS

| | | |
|---|---|---|
| 3,168,983 | 2/1965 | Bosak .................................. 239/211 |
| 3,895,928 | 7/1975 | Moran .................................. 239/136 |
| 3,908,905 | 9/1975 | Von Philipp et al. ................. 239/57 |
| 4,035,451 | 7/1977 | Tringali ................................. 261/30 |
| 4,166,087 | 8/1979 | Cline et al. ............................ 261/30 |
| 4,383,951 | 5/1983 | Palson .................................. 261/30 |
| 4,396,557 | 8/1983 | DeLuca ................................ 261/30 |
| 4,666,638 | 5/1987 | Baker et al. ........................... 239/57 |
| 4,695,435 | 9/1987 | Spector ................................. 239/54 |
| 4,743,406 | 5/1988 | Steiner et al. ......................... 239/60 |
| 4,752,423 | 6/1988 | Wong .......................... 261/DIG. 48 |

Primary Examiner—Tim Miles
Attorney, Agent, or Firm—Woodling, Krost and Rust

[57] ABSTRACT

The fragrance dispenser of this invention incorporates a service life indicator for the battery along with a fragrance pack having a service life equal to the service life of the battery, such that both the battery and fragrance pack can be easily and simultaneously maintained.

1 Claim, 4 Drawing Sheets

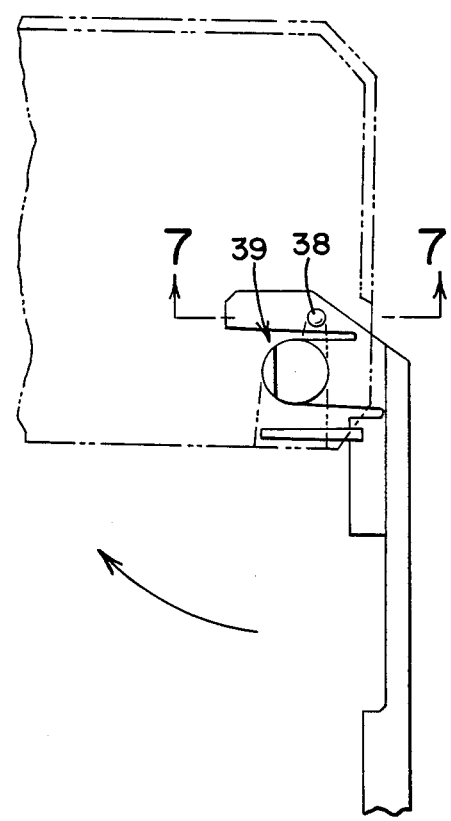
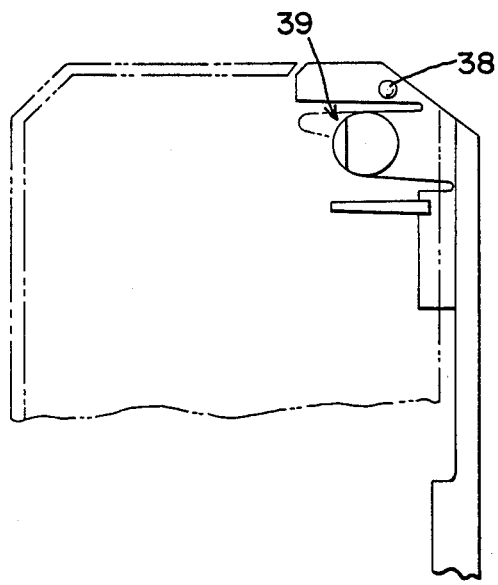
FIG. 7
FIG. 5
FIG. 6
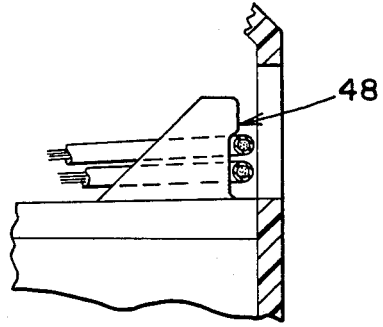
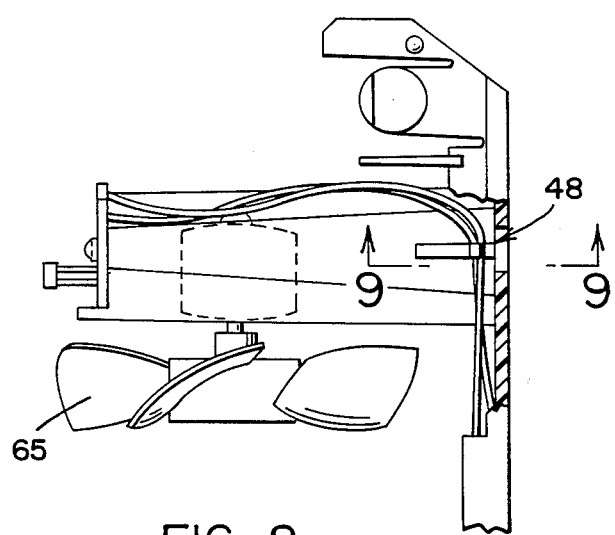
FIG. 9
FIG. 8

FRAGRANCE VAPOR DISPENSER MOUNTING BRACKET

FIELD TO WHICH INVENTION RELATES

Fragrance dispensers have become increasingly popular for air freshening, air deodorizing, air sanitation and the like. At present, the trend is toward convenience and flexibility of operation.

This Invention relates to an improved air freshener. It is especially suitable for use in commercial establishments needing a reliable, low maintenance frangrance dispenser, such as hospitals, warehouses, rest rooms, lounges, restaurants, and the like.

The preferred embodiment of the invention uses a bladed fan attached to the motor to circulate the air through the dispenser. The fan itself is operated by a non-line power source designed to run on either a continuous basis or on an intermittent basis. Operation of the fan may be controlled by an outside light source directed to the photo-electric cell, attached to the circuit board. The preferred design of the invention allows for the battery and the fragrance pack material to dissipate or expire at approximately the same time. This allows maintenance and replacement on a regularly scheduled basis or upon demand, signaled in the preferred embodiment by the extinguishment of the light-emitting diode (L.E.D.) which shows through the intake vent (21) on the frontal portion (25) of the cabinet (11). (The L.E.D. extinguishing upon depletion of the battery in the dispenser, a depletion preferably coextensive with the depletion of the fragrance pack.)

OBJECTS OF THE INVENTION

It is an object of this Invention to lengthen the service life of fragrance dispensers.

It is an object of this Invention to lower the operations cost of fragrance dispensers.

It is an object of this invention to lower the maintenance cost of fragrance dispensers.

It is an object of this invention to improve the adaptability of fragrance dispensers.

Other objects and a more complete understanding of the invention may be had by referring to the drawings in which:

DRAWINGS

FIG. 5 is a side view of the upper portion of the fragrance dispenser of FIG. 1 in a closed position showing a detail of the lock-open ratchet mechanism;

FIG. 6 is a side view of the fragrance dispenser as shown in FIG. 5 in a locked-open position;

FIG. 7 is a detail of FIG. 6 showing the lock-open ratchet in the locked-open position;

FIG. 8 is a side view of the upper position of the fragrance dispenser of FIG. 1 showing the wire storage assembly;

FIG. 9 is a detail of FIG. 8 showing the wire storage assembly;

SPECIFICATION

Figure 1:
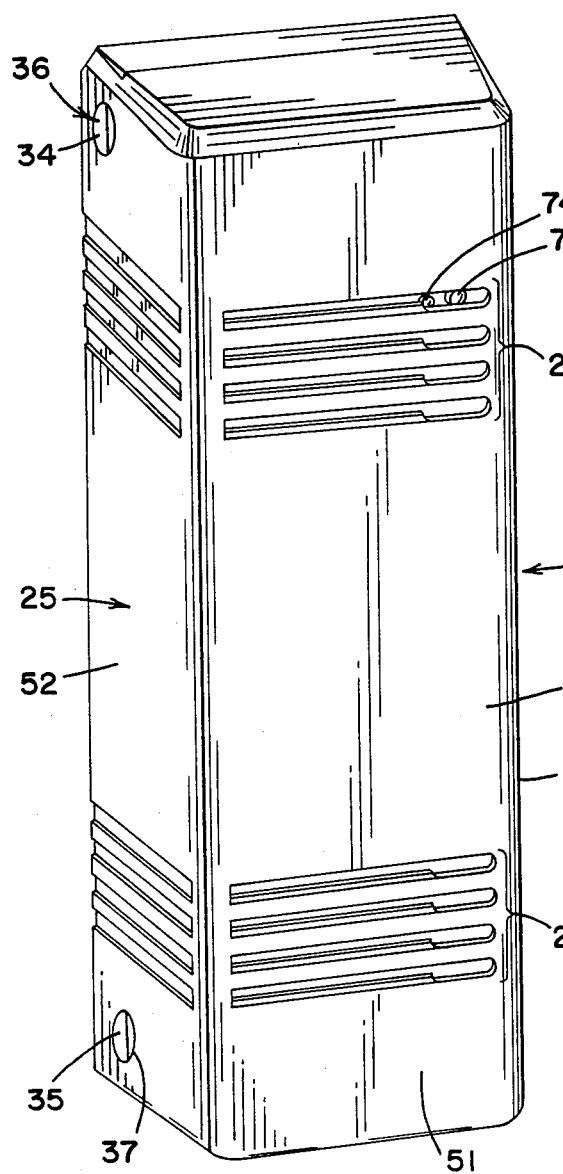
FIG. 1 is a perspective view of a fragrance dispenser incorporating the invention of the application.
Figure 2:
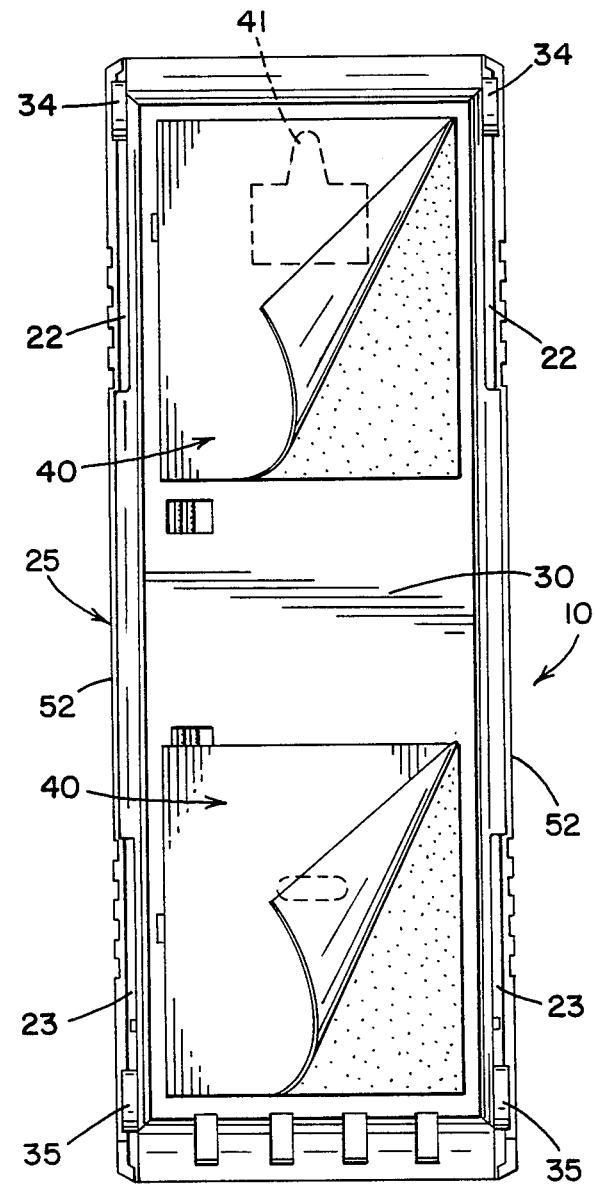
FIG. 2 is a back view of the fragrance dispenser of FIG. 1.

This invention relates to an improved fragrance dispenser (10). In the preferred embodiment disclosed the dispenser (10) includes a cabinet (11), a fragrance pack (12), a motorized fan (13) and a battery (14). The invention is adapted to be used with a gel-packed fragrance material (12) ("Gel-Pak" or "fragrance pack"), which is a volatile and vaporizing substance that can be activated by opening the top portion of the fragrance pack package. The material, being volatile, vaporizes when a current of air is passed directly over it.

The cabinet (11) is an enclosure having spaced intake vents (21) and discharge vents (20) on the upper and lower portions respectively of the front cover piece (25) of the Dispenser (10). Additional intake vents (22) and discharge vents (23) are formed by the joining of the front cover piece (25) and the back frame (25). The cabinet (11) can be oriented in any direction. In the preferred embodiment shown, the cabinet (11) is an injection molded two-piece plastic upright rectangular housing. One part of the cabinet (11), the back frame piece (24), serves as the mounting and retention member while the other part of the cabinet (11), the front cover piece (25), serves as the air pathway definition member.

The back frame-piece (24) includes a back (30), a motor mount (31), fragrance pack mounting brackets (32), a battery socket (33), pivot pins (34), closure locking pins (35), and lock-open pins (38).

The back (30) of the frame piece (24) serves to mount the fragrance dispenser (10) onto a wall or other surface. In the embodiment shown, the back (30) is preferably glued to the wall via two double-sided sticky tape patches (40). (Other mounting means could also be used. For example, the preferred cabinet (11) shown includes an alternate mechanical recessed eye (41) for use with a headed nail extending from the wall.) In the embodiment shown, the top of the cabinet (11) is included as part of the back (30).

The motor mount (31) of the frame piece (24) serves to mount the motorized fan (13) (later described) within the fragrance dispenser (10). The preferred embodiment shown utilizes a push fan having a downward air path for air circulation through the cabinet (11). The motor mount (31) is, therefore, located in the upper section of the back frame piece (24). The motor mount (31) itself has a generally rectangular shape with protruding end walls (42). The motor (66) of the motorized fan (13) fits within the motor mount (31) with the end walls (42) protruding beyond the motor. The distance between the upper and lower (not shown) walls (43) of the motor mount (31) is substantially equal to the axial length of the motor. These upper and lower walls (43) serve to support the motor against upwards and downwards movement. Semi-circular indents in the center front edge of the walls (43) serve to retain the motor against sidewards movement. A circuit board (45) (later described) is mounted at the tip of each of the end walls (42) of the motor mount (31) by means of an extension of these end walls (44) which fit into corresponding holes on the circuit board (45). In addition to its electronic function, the circuit board (45) in the preferred embodiment also insures the retention of the motor onto the motor mount.

The fragrance pack mounting brackets (32) serve to mount the fragrance packs (12) onto the frame piece

(24) within the air path. Since the preferred embodiment shown utilizes a push fan providing a downward air path, the fragrance mounting brackets (32) are located beneath the motor mount (31). The mounting brackets (32) are designed to match the fragrance packs (12) (later described). Since the preferred fragrance packs shown are generally square with two side inset portions, each mounting bracket (32) includes two engaging arms (46) extending forwardly and upwardly (for engaging the side lips of the packs) and a central stabilizing pocket defined by brackets (47) (for engaging the inset portions of the pack). This specifically designed mounting system enables the user to unambiguously replace the fragrance packs by feel as for example, in the unit which may be located in a dark or an out-of-the-way place. The extra stability of the preferred mounting also helps to prevent the fragrance packs from spilling the liquid portion of their contents within the unit itself.

The battery socket (33) serves to mount the battery onto the frame piece (24). In the preferred embodiment a single "D" sized battery (14) is utilized. The battery socket (33) is, therefore, designed to fit this sized battery including the necessary electrical contacts (50). The preferred battery socket is strategically located below all operable parts so as to reduce potential damage in the event of battery leakage. This will reduce harmful damage to the internal componentry of the Invention in the event of battery or fragrance pack leakage.

Figure 3:
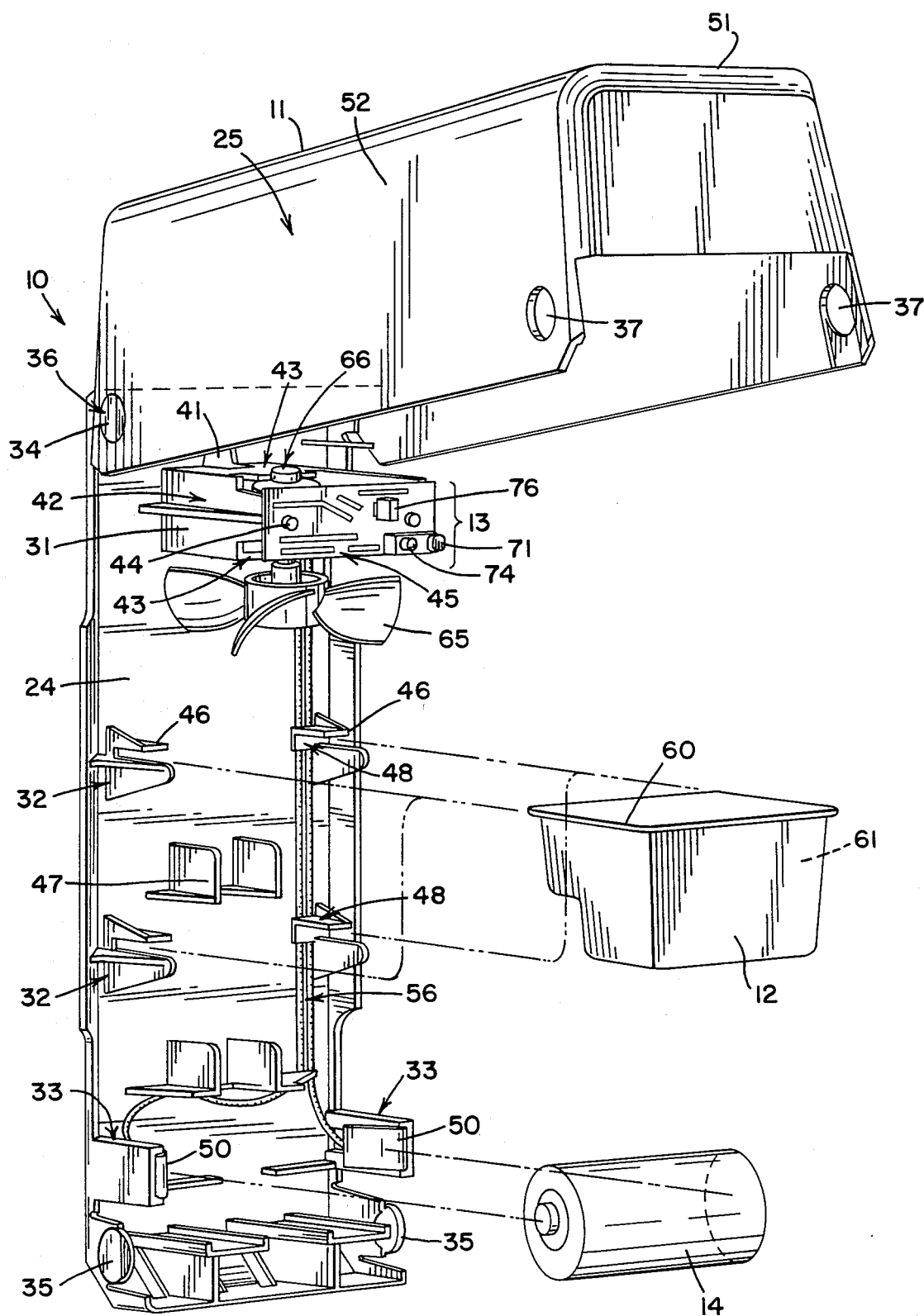
FIG. 3 is a perspective view of the fragrance dispenser of FIG. 1 with an open cabinet.

The invention is hinged to open vertically by means of pivot pins (34). The pivot pins (34) are part of the molded plastic frame (24) and are located on either side of the upper section of the back frame piece (24). These pins (34) (normally non-releasable) extend into two matching holes (36) in the top of the front cover piece (25) (later described) to pivotally join the front cover piece (25) to the back frame piece (24). Once joined, the front cover piece (25) can be rotated from a downward closed position (FIG. 1) to an upward open position (FIG. 3). Two closure locking pins (35) which are part of the bottom of the molded plastic frame (24), releasably fit into two matching holes (37) in the bottom of the front cover piece (25) (later described) to retain the front cover piece (25) in its closed downward position.

The preferred embodiment of the invention contains two lock-open pins (38) on the back frame piece (24) (FIG. 5). These pins extend into two matching grooves (39) in the top of the front cover piece (25) to selectively lock open the front cover piece (25) (FIG. 6). The pins are releasable for easily closing the unit after servicing. The lock-open pins (38) themselves lock into place upon rotation of the front cover piece (25) for a certain number of degrees. With a lesser rotation, the pins (38) have no effect on the movement of the front cover piece (25). The user of the dispenser (10) can, therefore, pivot the front cover piece (25) for a lesser number of degrees without engaging the lock-open pins (38). This allows for a quick flip up and return movement of the front cover piece (25) (for visually checking on the device, minor maintenance, battery replacement, etc.) while also allowing for latch up upon engagement of the pins (38) (for cleaning, major maintenance, etc.). The number of degrees that latch-up occurs is selected with a view towards the specific need for the particular Dispenser (10). In general, the greater the need for long term access, the easier it will be to engage the pins (38).

The front-cover piece (25) serves as the main air guide for the Fragrance Dispenser (10). In the embodiment shown, the air flow for the device is generally downward over the fragrance packs (12) from an upper motorized fan (13). To guide this air, the cover piece (25) has a front (51) and two side walls (52). These walls (51 & 52) serve to channel the air from the fan over the fragrance packs (12) before discharge. The four (4) air intake vents (21) are located in both walls of the front-cover piece (25) at or above the level of the motorized fan (13). The four (4) air discharge vents (20) are located in the front-cover piece (25) at or below the level of the open fragrance dispensing sections of the fragrance packs (12). The same configuration applies to the additional air intake vents (22) and additional air discharge vents (23). The location of these vents (20, 21, 22, and 23) insures the passage of air over the fragrance packs (12) before discharge. The user can determine the desired strength of fragrance by varying the speed/pitch of the fan, by using one or more fragrance packs (12), by varying the exposure of the fragrance packs (12), by using fragrance packs (12) of varying volatility (partially or fully open for example), or otherwise. The air flow is designed to optimize the desired fragrance level and the life of the fragrance material.

The fragrance pack (12) is the source of the fragrance or other dispensable material. The actual type of source (liquid, Gel-Pak, solid, etc.), its volatility and number would depend upon the type and nature of the dispensable material (along with the other design parameters of the dispenser (10)). In the preferred embodiment disclosed, the fragrance packs (12) are generally square shaped, open-top plastic cups (60) containing a volatile and vaporizing gel-packed fragrance material (61). The lipped cups (60) are approximately $1\frac{3}{4}'' \times 1\frac{1}{2}'' \times 1\frac{3}{4}''$ with two $\frac{5}{8}'' \times \frac{5}{8}'' \times \frac{1}{2}''$ cutouts inset into the back lower edge thereof.

After manufacture and before usage, the top of the cups (60) are covered by a selectively removable, peelable cover (not shown). This cover seals the fragrance material (61) into the cups (60) during storage. The pre-sealed fragrance can, therefore, be stored for long periods of time allowing the user to stock additional fragrance packs for months or even years in advance of actual usage.

To use the cup (60), the top of the cup (60) is punctured or removed to expose the fragrance material (61). The cup (60) is then placed onto the fragrance pack mounting brackets (32) within the cabinet (11). The upper lip of the cup (60) engages the lip engaging arms (46) and the cutout inset back edge of the cup (60) engages the central stabilizing pocket (47). This three point contact provides for a stable mounting. Note that the preferred embodiment shown has two sets of mounting brackets (32). This allows a second cup (60) to be located within the cabinet (11) for storage (unopened) or tandem use (open). The storage is convenient; the tandem use allows one to increase or vary the dispensable material within a given dispenser (10). This configuration would also permit a double-depth fragrance pack container to be inserted into the dispenser (10). This longer lasting fragrance pack would be ideally suited for use with a longer life battery (for example, heavy-duty or alkaline-type "D" cell battery) in a dispenser, otherwise, designed for a regular battery. Some users would prefer this longer life, although the cost of such usage would be higher.

The actual fragrance used with the dispenser (10) is selected to match the intended application. This would include anything dispensable from a roach killer, to a masking odor, to an air fresher or otherwise. The volume, volatility, surface area and other parameters are selected in combination with battery life to optimize the operation of the dispenser (10) (The subsequently described control circuit optimized this life). With multiple containers, differing volume, or other changes, a single dispenser (10) could have multiple uses. In the preferred embodiment disclosed, the fragrance is an air freshener having a 30-day life assuming 12 hour on/12-hour off fan operation per day (see FIG. 10) and a 45-day life assuming an 8-hour on/16-hour off fan operation per day (fan operation later described). The adaptability of the invention, however, makes it ideally suited for almost any application.

The motorized fan (13) is an air circulation mechanism for the dispenser (10). In the preferred embodiment disclosed, the fan (13) forces the passage of air between the intake vents (21), (22) and discharge vents (20), (23) over the fragrance packs (12). The fan (13) itself includes a four blade, two and one-half inch diameter blade (65) rotated by a 1.5 volt D.C. Motor (66). The location of the fan blade (65) underneath the motor (66) and above the fragrance pack(s) (12) allows free movement of air within the cabinet (11) without interference from the motor (66) or from other internal elements. The mounting of the motor (66) to the mounting brackets (31) of the cabinet (11) has been previously described. The particularized configuration of the cabinet (11) itself creates an airflow pattern that optimizes the emission of fragrant air during selected time intervals. The downward air flow, directly over the opened fragrance pack(s) (12), fully impregnates the air during the desired use period.

Figure 4:
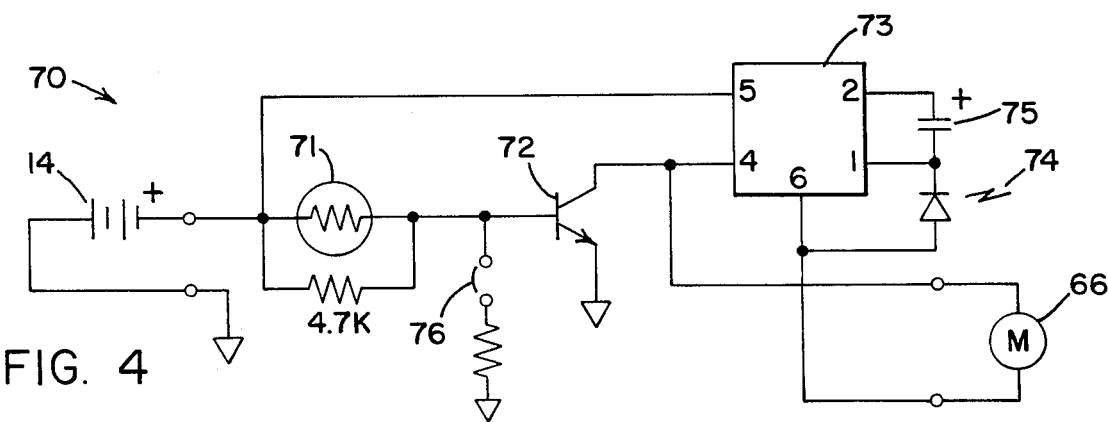
FIG. 4 is a circuit diagram of the control circuit for the fragrance dispenser of FIG. 1.

The motor (66) of the fan (13) is controlled by an electronic circuit (FIG. 4) for optimum battery life. In the eletronic circuit (70) a light sensitive photocell (Phelox VT 902) (71) triggers a transistor (2N 4401) (72) to energize the motor (66) (1.2 low voltage, low current) and an operations control integrated circuit (LM 3909) (73). A removable bypass (76) (dip-shunt) allows for constant fan operation if desired. The motor (66) rotates the fan (13). The operations control (73) flashes a light emitting diode (L.E.D.) (HLMP1700) (74) to indicate correct operation. The speed at which the L.E.D. (74) flashes is controlled by the capacitor (I-22 UFRLGV) (75). This speed is not critical. The speed preferably is such as to provide a quick indication of the operability of the unit without also being distracting to the users for the room containing the dispenser.

The design of the electronic circuitry is particularly suited to the control of this dispenser. For example: The integrated circuit (73) is designed to allow the unit to continue working even when the battery (14) is generating less than one volt of current. Additional example: The L.E.D. (74) was selected for this application since it will continue to run in a low voltage situation, whereas, most other L.E.D.'s will not operate at less than 2.2 to 2.3 volts. A possible alternative to the selected L.E.D. (74) which is a Hewlett-Packard (HLMP1700), is an L.E.D. manufactured by General Instrument (GL1700). Futher example: The Phelox VT 902 photocell (71) is suited to operate in conjunction with the removable bypass (76).

Note that the particular preferred control circuit is disclosed itself by way of example and not for limitation of the invention; other control circuits could also be utilized. For example: If the dispenser (10) was going to be utilized in a completely dark closet, then internal photocell operation would not be appropriate—a timer circuit, a remote photocell, or air movement sensor operation, etc. would be more suitable. Additional example: Due to regional parts availability, a differing circuit having a similar result to the preferred control circuit could be utilized. These differing control circuits would all preferably be optimized for the given application in combination with the other variables within the dispenser (10).

The photocell (71) and the L.E.D. (74) of the preferred control (73) are preferably exposed to the exterior of the cabinet (11); the photocell (71) to allow more efficient operation; the L.E.D. (74) to ease maintenance checks. In the embodiment disclosed, this exposure occurs by having both the L.E.D. (74) and photocell (71) located adjacent to the intake vent (21) for visibility therethrough. The location of the circuit board (45) containing the control (70) at the end of the motor mounts (42) allows for this convenient location without the necessity of mounting these elements on the front cover piece (25) itself. It also allows for convenient replacement/exchange of the control circuit. The integrated circuit board and electric-fan motor are connected to the power source by means of two wires (56), which run vertically from the top of the unit to the bottom of the unit, where the power source is located. The wires are secured out of the way by means of two clips (48) created by the right arms of the mounting brackets (32) used for the fragrance pack materials (12), to provide an out-of-the-way path for the wires. This allows easy maintenance and cleaning. (See FIGS. 3, 8, and 9).

Figure 10:
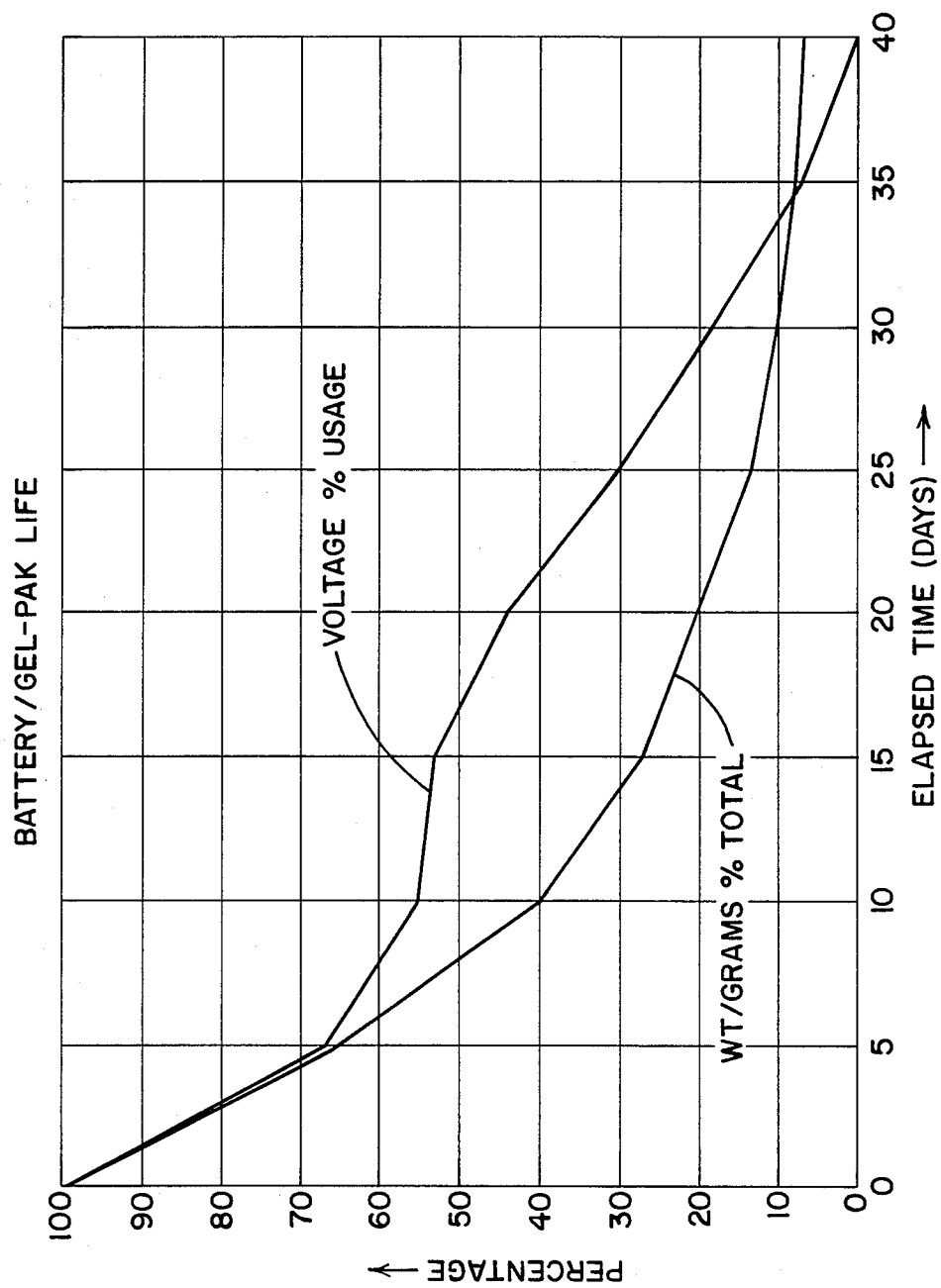
FIG. 10 is a graph of battery and fragrance pack reserve vs. time for the fragrance dispenser of FIG. 1.

The electronic circuit (70) effectively lengthens the service life of the battery (14) and fragrance pack (12) of the dispenser (10). In the preferred embodiment disclosed, a standard "D" sized battery (14) without the selective photocell operation of the circuit (70) has a service life of approximately 19 days (the end of service life defined as being a battery voltage of somewhat less than 1.2 volts under load, the voltage necessary to operate the motor (66) through the circuit (70). (A heavy duty battery has a service life of 23 days, and alkaline battery 38 days under the same parameters). With the selective operation of the circuit (70), the service life of a standard "D" sized battery (14) is extended to approximately 38 days or nearly double that otherwise obtainable assuming 12-hour on/12-hour off operation as shown in FIG. 10. With a more restricted eight hours per day, the standard "D" sized battery would have a service life of approximately 50 percent more. (The service life of the heavy-duty and alkaline batteries are similarly extended).

Note that the rate of battery voltage decline normally decreases after the initial few days unders all circumstances. The decreases is due to, in part, to the increasing significance of the recovery of the battery (14) during the off-periods of the motor (66). The amount of this recovery is too limited to be accurately reflected on the graph of this application (FIG. 10). A more detailed graph would reflect this recovery. The dispenser (10) is an integrated device. For this reason it is preferred that the fragrance pack (12) and battery (14) last as long as practical and, in addition, be amenable for service at approximately the same time. Of the two elements, it is more cost effective (and easier) to control the service life of the fragrance pack (12) than the service life of the battery (14) (High capacity batteries are expensive). It is also easier to recognize and signal the end of the service life of a battery than of a fragrance pack (12) (i.e. voltage not weight, opacity, volume, etc.). Therefore, the preferred embodiment utilizes standard off-the-shelf consumer batteries with the service life of the fragrance pack (12) designed to approximately match the service life of the battery (14). The service life of the standard "D" cell battery of the preferred embodiment has been extended by the control circuit (70) to over 30 days (12-hour on/12-hour off operation) and 45 days (8-hour operation) (heavy-duty and alkaline batteries have a similar percentage increase). The service life of the fragrance pack (12) is, therefore, designed to approximately match or slightly exceed the service life of this battery (the service life of the fragrance pack (12) is preferably, slightly more than the battery (14) to insure that the fan (13) always has a fragrance material to circulate air over). In the preferred embodiment of this application, a full container of fragrance (100 grams=100%) has a sufficient volatility to last for the same time as a fully changed "D" cell battery (1.5 volts=100%) with the same 12-hour on/12-hour off operation (FIG. 10). The curve of the fragrance has a significant percentage drop in the first few days (as the more volatile elements escape) with a considerable leveling off at the tail end of the service life (as fewer volatile elements are available to escape). The leveling-off at approximately 17 grams or 7.5% of the total weight marks the effective end of the service life of the fragrance pack (12). By designing the service life of the fragrance pack (12) to approximately equal the service life of the battery (14) (1.22 volts or 6.5% of usable voltage being the effective end of the service life of the standard "D" cell battery), both items can be serviced at the same time. This allows for a single uniform maintenance schedule. In the preferred embodiment, this event is conveniently indicated by the fact that the L.E.D. (74) stops flashing. Both the fragrance pack (12) and the battery (14) will be expended after approximately 30 to 35 days. Therefore, the maintenance person need only glance at the intake vent hole (21) of the frontal portion of the unit (25) once each month to determine whether the L.E.D. (74) is flashing. If the L.E.D. is flashing, both the battery and fragrance pack are at acceptable operational levels. If the L.E.D. is not flashing, both the battery and fragrance packs should be replaced. Note that the change from a standard to an alkaline "D" battery would effectively double the service life of the battery. This interchange is very easy to make; cautionary instructions would be given to the operator of the Dispenser (10) of the importance of matching a cup (60) with a battery of a suitable service life. These instructions could be in the cabinet (11) (for example, "use standard D-cell batteries only"), on the cup (60), or otherwise. For a Dispenser (10) utilizing differing batteries, it is preferred to mark the cup (60) with an indication of suitable battery type; the cup (60) defines what type of battery it is designed to match. Alternately, one could sell (for example, "for use with standard D-cell batteries") matched battery and fragrance pack sets including the proper combinations (along with an indication of designed service life). When used in tandem with the fragrance packs (12) which are designed for even, efficient evaporation over the same service life, the use of the proper batteries makes the object of this Invention very economical to use. If desired and to avoid consumer complaints about unmatched service life, the fragrance packs (12) could be designed to have an increased residual fragrance production level that continues after the expiration of its normal service life—i.e. the material in the cup (60) retains some increased level of ability to produce fragrance after the end of a 30-day period for a standard "D" battery (14) than that normally expected. This increased residual level would provide at least a measure of functioning if the consumer used a longer service life battery—i.e. mismatched a standard "D" battery cup (60) with a heavy-duty battery. This functioning would aid in consumer relations for no company likes to inform a customer that, that customer did not follow the instructions for a device.

The battery (14) supplies the power for the motorized fan (13). As previously discussed, the source of power is not important except for the matching of service life.

Although this invention has been described in its preferred form with a certain degree of particularity, it is to be understood that numerous changes may be made without departing from the claimed invention. For example, the dispenser (10) has a vertical opening cabinet (11) with a downward air flow from a push fan between sideward vents. The dispenser (10) could equally well have a horizontal non-opening cabinet with a side-to-side air flow due to a push fan between end openings or other type of cabinet and air flow. Similarly, the electronic circuit has an integrated circuit with indicator L.E.D. These could be eliminated and another control circuit substituted. In addition, the fragrance pack (12) is described as an open container. The pack (12) could, in fact, be any source of fragrance—even a valved spray container. Other changes are also possible without departing from the invention as claimed.

We claim:

1. In a fragrance dispenser having a fragrance pack mounting onto a cabinet, the improvement of the fragrance pack having two laterally disposed sidewards extending upper lips and a cut out inset back edge and said mounting including three brackets, two for the laterally disposed upper lips respectively and one for the inset back edge of the fragrance pack.

* * * * *